United States Patent [19]

Griffin

[11] Patent Number: 4,678,579
[45] Date of Patent: Jul. 7, 1987

[54] DISPOSABLE UNITARY CYTOLOGY CHAMBER AND FILTER CARD FOR CENTRIFUGATION OF FLUID SAMPLES AND METHOD OF MAKING SAME

[75] Inventor: Daniel V. Griffin, Denver, Colo.

[73] Assignee: Whale Scientific, Inc., Commerce City, Colo.

[21] Appl. No.: 678,262

[22] Filed: Dec. 5, 1984

[51] Int. Cl.⁴ .............................................. B10D 23/00
[52] U.S. Cl. .................................. 210/477; 210/782; 422/104; 128/760; 604/DIG. 704
[58] Field of Search ............... 210/361, 451, 472, 477, 210/781, 782, 330, 321.1, 436, 455, 436, 451; 422/104, 101, 68, 72; 128/760, 767, 771; 604/DIG. 704

[56] References Cited

U.S. PATENT DOCUMENTS

| | | | |
|---|---|---|---|
| 4,062,781 | 12/1977 | Strauss et al. | 210/451 |
| 4,137,573 | 6/1979 | Kroeger | 128/760 |
| 4,265,762 | 5/1981 | Brenholt | 210/451 |
| 4,344,562 | 8/1982 | Riichi | 233/26 |
| 4,357,240 | 11/1982 | Mehra et al. | 422/101 |
| 4,391,710 | 7/1983 | Gordon | 422/101 |
| 4,448,207 | 5/1984 | Parrish | 128/771 |

Primary Examiner—Andrew H. Metz
Assistant Examiner—Sharon T. Cohen

[57] ABSTRACT

A unitary disposable chamber and filter unit including a method for making same in which a support surface on the chamber has energy directors such that when ultrasonic energy is applied thereto the energy directors will become molten and bond a filter card to the support surface at spaced locations away from the point of discharge of the fluid through the filter card onto a microscopic slide or other surface for analysis.

16 Claims, 9 Drawing Figures

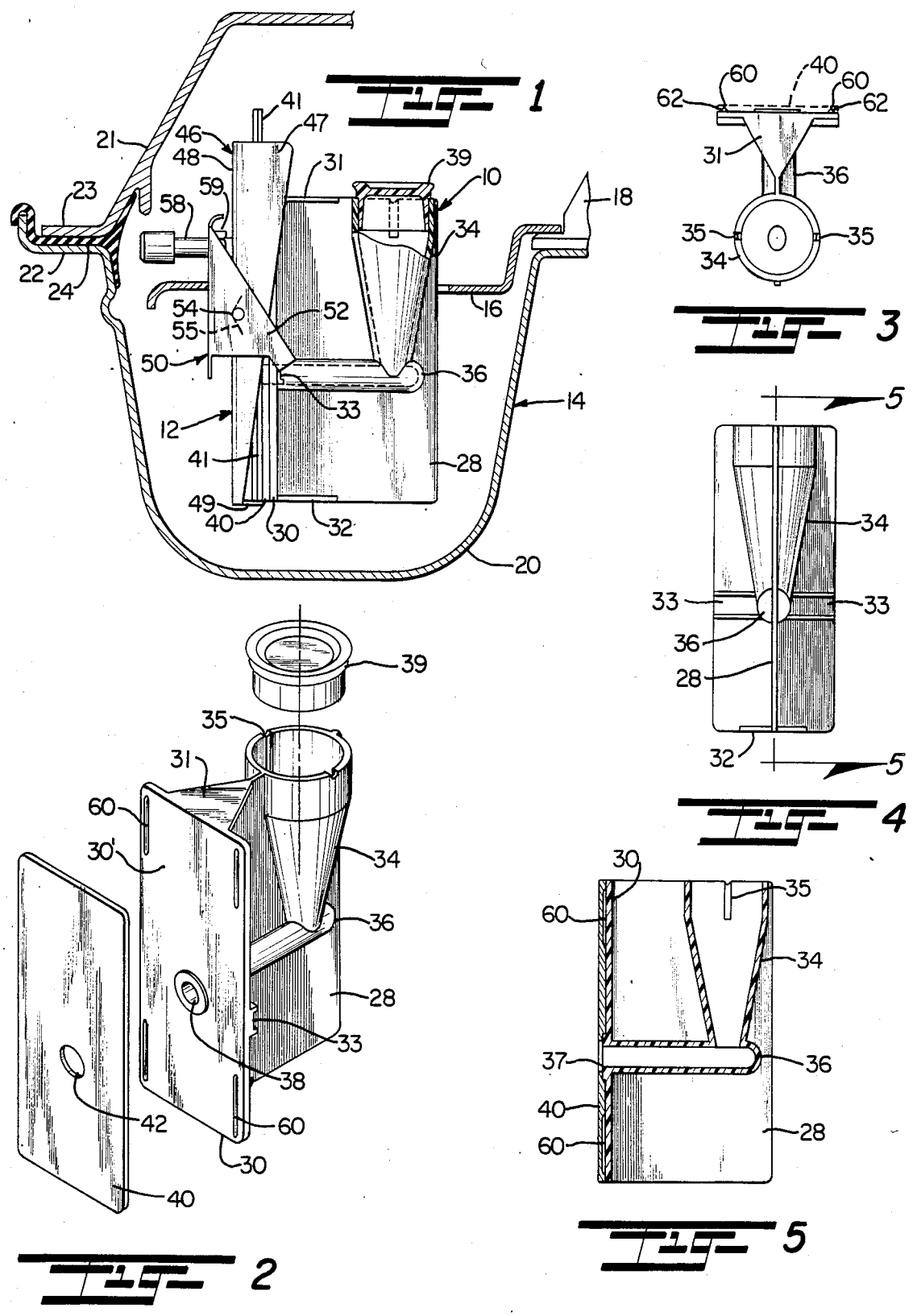

DISPOSABLE UNITARY CYTOLOGY CHAMBER AND FILTER CARD FOR CENTRIFUGATION OF FLUID SAMPLES AND METHOD OF MAKING SAME

This invention relates to filter assemblies for use in the analysis of body fluids; and more particularly relates to a novel and improved unitary cytology chamber and filter card and to a method for making same for use in the centrifugation of body fluid samples.

BACKGROUND AND FIELD OF THE INVENTION

Centrifuges are customarily employed in the separation of cells and other solids from body fluids to permit subsequent diagnosis or analysis. Centrifuges presently in use are designed to accommodate a plurality of sample chambers and in such a way as to be capable of rapidly loading and unloading the chambers so as to facilitate more rapid and efficient sampling. One such centrifuge is the cytocentrifuge set forth and disclosed in U.S. Pat. No. 4,391,710 to A. J. Gordon wherein a plurality of holders are arranged in spaced circumferential relation to one another about a common motor drive, each holder adapted to retain an individual chamber together with a separate filter card and slide. Specifically, each holder is made up of a channel adapted to receive a slide which is overlaid by a filter card and by a correspondingly shaped end flange at an end of the sample chamber. The holder includes a clamp in order to retain the assembly of the chamber, filter card and slide together and in properly aligned relation such that the filter card will properly absorb the liquid component of the sample and permit the cells and other solids to pass through the card and be deposited onto a surface of the slide.

As noted in the hereinbefore referred to patent to Gordon, the problem associated with prior art arrangements is the assembly operation to be carried out in the installation of the sample chambers in conjunction with the rotating carrier of the centrifuge and specifically to achieve proper alignment between the chamber, filter card and receiving surface of the slides. Such arrangements in the past have been difficult to assemble and manipulate especially when the material being centrifuged must be handled under conditions of containment in order to prevent the escape of toxic or noxious matter. Nevertheless, in accordance with the teachings of the patent to Gordon, it is necessary to preassemble each chamber, filter card and slide as a preliminary to mounting in the holder. Upon completion of the centrifuge operation, removal of the assembled components and disassembly of same to recover the sample to be examined, the holders and chambers must then be cleaned and sterilized individually for subsequent reuse.

Notwithstanding that the centrifuge disclosed in the patent to Gordon offers definite advantages and improvements over the prior art in the handling and sampling of body fluids, there exists the need for a unitary cytology chamber and filter card assembly which not only minimizes the steps of preassembly with the microscopic slide or glass as a preliminary to placement in the holder, but assures accurate alignment between the elements and, most importantly, precludes reuse of the chamber and filter card. The latter is particularly important in the handling of body fluids containing certain diseases where it is vital that the chamber of filter card not be reused after a particular sampling operation. Joining of the two components together as a unitary assembly avoids any temptation on the part of the operator to reuse either or both in subsequent sampling operations. It is therefore proposed to provide a unitary chamber and filter card in which the components are permanently united together in properly aligned relation and cannot be separated without destroying the interface between the two; yet in uniting the two together avoids any danger of contamination of the sample and offers an extremely simple but effective way of assembling the components so as to prevent their reuse and assure more rapid loading and unloading of the samples with respect to their respective holders.

Other representative U.S. Letters Patent in this field are U.S. Pat. No. 4,265,762 to D. L. Brenholt; U.S. Pat. No. 4,344,562 to A. Ricci; and U.S. Pat. No. 4,357,240 to R. C. Mehra et al. However, none suggests or discloses a manner and means by which a filter card may be permanently affixed to an end flange on a chamber and in properly aligned relation so as to form a disposable unit and in such a way as to preclude reuse of the assembly in the manner devised according to the present invention.

SUMMARY OF THE INVENTION

It is therefore an object of the present invention to provide for a novel and improved disposable cytology chamber for use in analysis of liquid samples.

Another object of the present invention is to provide for a novel and improved method and means for fabricating a unitary, disposable cytology chamber and filter card so as to prevent reuse of the chamber together with a vented cap to prevent spillage of liquid during centrifuge operations.

It is a further object of the present invention to provide for a novel and improved method of integrally uniting a filter card to a flat end surface or flange of a chamber in such a way as to avoid the possible contamination by use of adhesives to other securing means and to assure reliable performance in operation.

It is an additional object of the present invention to provide for a novel and improved method of ultrasonically welding a filter card to a flat end surface of a disposable chamber unit in such a way as to avoid contamination of a fluid sample to be analyzed and to prevent reuse of a unit.

In accordance with the present invention there has been devised a cytology chamber characterized by having a funnel-shaped portion and communicating discharge port which extends through an end flange, and a filter card is permanently affixed to the exposed end surface of the flange with an opening in the filter card properly aligned with the discharge port. The end surface is characterized by having special attachment means to facilitate permanent attachment of the filter card to the end surface without in any manner altering the characteristics of the filter card itself for its intended purposes. In the method of the present invention, a filter card is permanently affixed to a flat end flange of a cytology chamber wherein the chamber has a funnel and discharge port which intercommunicates between the funnel and end flange, the steps comprising forming energy directors in the form of protruding ribs on the exposed surface of the end flange and ultrasonically welding one surface of the filter card whereby to embed and fix the energy directors in the card at selected spaced intervals away from the discharge port while assuring that the card will be disposed in flush relation to the end flange and conduct liquid by absorption away from the discharge port when the chamber is subjected to centrifugal forces.

In a preferred embodiment, the cytology chamber and attached filter card are combined with a microscopic slide which is applied in flush relation to the filter card and releasably clamped in a holder of a cytocentrifuge. The cytology chamber is of the type having a generally funnel-shaped portion disposed on a longitudinal axis parallel to the axis of rotation of the centrifuge, a releasable cap usable in combination with vents in the funnel and a discharge port at one end of the funnel extending radially away from the funnel into communication with the end flange. Thus, when a liquid sample is placed in the funnel and subjected to centrifugal forces it will be constrained to flow outwardly through the discharge port where the liquid component of the sample is absorbed by the filter card and any solid matter is collected on a surface of the slide. The chamber and slide are then released from the holder and the specimen on the slide subjected to diagnosis or analysis in a conventional manner. The permanent attachment of the filter card to the end flange of the chamber is such that any attempt to remove the filter card will result in leaving substantial segments of the card in attached relation to the energy director and prevent replacement with another card.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a cross-sectional view illustrating the disposition and mounting of a preferred form of chamber and filter card assembly in a cytocentrifuge in accordance with the present invention;

FIG. 2 is an exploded view of preferred form of cytology chamber and filter card preliminary to ultrasonically welding the filter card to the end surface of the chamber;

FIG. 3 is a top plan view of the assembled cytology chamber and filter card as shown in FIG. 2;

FIG. 4 is a front view of the cytology chamber and illustrated in dotted form the placement of energy directors on the end surface thereof;

FIG. 5 is a cross-sectional view taken about lines 5—5 of FIG. 4;

DETAILED DESCRIPTION OF THE PREFERRED EMBODIMENT

Figure 6:
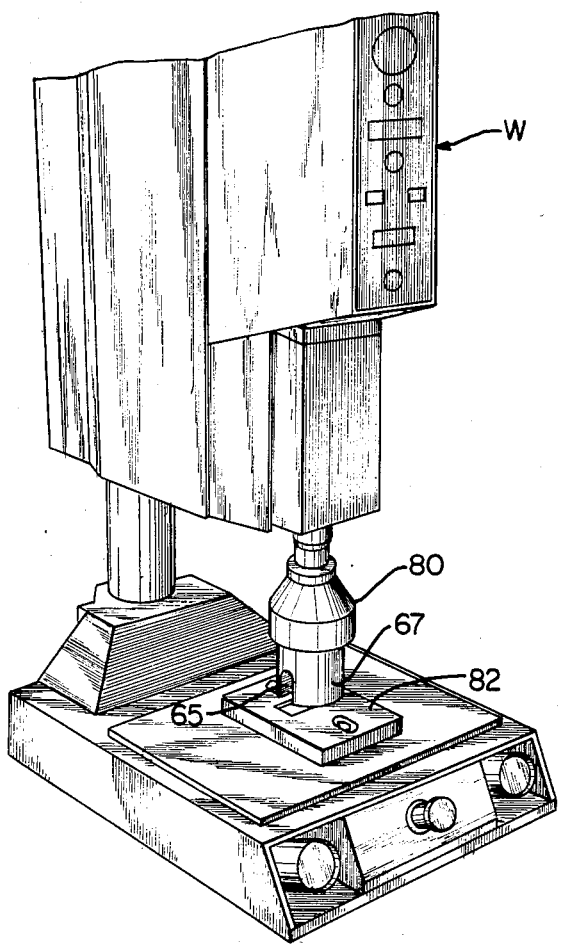
FIG. 6 is a somewhat perspective view illustrating a welding unit employed in assembling a filter card and cytology chamber together.

Referring in more detail to the drawings, there is shown by way of illustrative example in FIG. 1 a preferred form of chamber and filter card assembly 10 installed in a holder 12 of a cytocentrifuge, a portion of which is generally designated at 14. As a setting for the present invention, the centrifuge 14 comprises a series of holders 12 which are mounted in spaced circumferential relation in a common carrier plate 16 which is disposed for rotation about a vertical axis through a central drive unit including a hub, a portion of which is represented at 18. For purposes of illustration, the drive unit may be suitably comprised of the central hub 18 mounted on the output shaft of a drive motor, and the carrier plate is fixed for rotation to the hub 18. The holder assemblies 10 and carrier plate 16 are suspended within a lower bowl portion 20 and upper cover 21 with mating peripheral edges 22 and 23 of the bowl 20 and cover 21 interconnected and a seal 24 being interposed therebetween.

As a preliminary to describing the construction of a typical holder 12, it should be noted that the preferred form of cytology chamber 10 comprises a main body in the form of a flat, generally rectangular plate 28 having an end flange 30 disposed normal to and along one edge of the plate 28 and which is reinforced by generally triangular, upper and lower ends 31 and 32, respectively. The front surface of the flange 30 is provided with horizontally directed, slotted ledges 33 on opposite sides of the plate 28 for a purpose to be described. A vertically directed funnel portion 34 is contained within the body and tapers downwardly into a laterally extending discharge port 36 which is directed from the lower end of the funnel through the end flange 30 and terminates in an opening 37 surrounded by an annular sealing surface 38 projecting from exposed end surface 30' of the end flange 30. A cap 39 is dimensioned for releasable insertion in the upper open end of the funnel, and release vents in the form of vertical slots 35 along the inner wall of the funnel permit the escape of air when the cap 39 is in place. A filter card 40 is dimensioned to be coextensive with the end flange 30 and is provided with a circular opening 42 which is located to register with the annular sealing surface 38 when the filter card is aligned with and permanently attached to the end flange.

Broadly, cytology chambers of the type described are designed such that a liquid sample may be placed in the funnel 34 and remain there until the centrifuging operation commences at which time the sample will be driven in a radial outward direction through the discharge port 36. For this purpose, the holder assembly 12 is constructed and arranged for releasable insertion and clamping of the chamber therein with the funnel portion 34 positioned radially inwardly of the end flange 30 and with the funnel 34 disposed in a generally upright position. The holder assembly 12 is comprised of a generally U-shaped channel 46 having opposite side plates 47, a common web 48 interconnecting the side plates, and a locating lug or end stop 49. A generally U-shaped clamping member 50 is disposed in surrounding relation to the midsection of the clamping member, the clamping member having opposite, generally triangular sidewalls 52 with inturned lugs 53 at the lower extremities of the sidewalls 52 to overlie the downwardly tapered sides 47 of the channel 46 and engage the ledges 33. A pivot rod 54 extends across the channel member 50 through the sidewalls 52 and is spring-loaded by a torsion spring 55 so as to permit rocking movement of the clamp 50 relative to the channel 46 in a manner to be described. A release screw 58 is threaded into a boss 59 on the clamping member 50 so that its leading end is engageable with the rear face of the web 48 of the channel to cause the clamping member 50 to rock or tilt about the pivot rod 54 in opposition to the torsion of the spring element 55 on the pivot rod.

In the installation of the chamber assembly into the holder assembly, a microscopic slide 60 is assembled or placed against the filter card 40. Preferably, the slide 60 is a rectangular glass slide dimensioned to correspond to the size of the filter card 40 and is inserted along with the filter card 40 and end flange 30 of the chamber by sliding downwardly through the channel 46 until the lower edges of the end flange 30, filter card 40 and slide 60 abut the forwardly directed end stop 49 at the lower edge of the channel 46. In this relation, the inturned lugs 53 will engage opposite sides of the end flange 30. In the inloading position prior to commencement of the centrifuging operation, while forming no part of the present invention, the release screw 58 in bearing against the channel member 46 will cause the chamber 10 and its funnel 34 to be tilted or tipped somewhat downwardly and the open end of the port to be tipped upwardly so that any liquid in the funnel which passes into the discharge port 46 will remain at the closed end of the port. Under rotation, the centrifugal force imparted to the holder will cause the holder and chamber assembly to rock back into a horizontal position as illustrated and simultaneously to force the liquid to flow from the funnel through the discharge port and through the matched openings at the open end of the discharge port and the filter card into direct contact with the exposed surface of the slide. The filter card will absorb any of the liquid contents of the sample while any solid matter will be deposited on the surface of the slide.

Having considered the manner in which the chamber assembly 10 is employed in the recovery of a sample, reference is now made in more detail to the construction and arrangement of the end flange 30 and filter card 40 and the method of joining or permanently affixing the filter card to the end flange. Referring specifically to FIGS. 2 to 5, the normally exposed end surface 31 of the end flange 30 is formed with narrow elongated ribs 60 which protrude a limited distance away from the end surface 31 and converge into tapered or pointed edges 62. Each rib 60 is located to extend in closely spaced parallel relation to opposite side edges of the end flange 31 and to protrude outwardly therefrom for a limited distance which is less than the thickness of the filter card 40. Similarly, the annular sealing flange or surface 38 is formed in surrounding relation to the open end of the port 36 and protrudes from the end surface a distance slightly greater than that of the ribs. Preferably, the ribs are formed out of the material on the end flange, each preferably being of a length of approximately one-fifth of the total length of the end flange and located relatively near the four corners of the end flange but away from the central opening. The ribs as described define energy directors to facilitate attachment of the filter card thereto when subjected to ultrasonic welding.

In the preferred method of joining the filter card 40 to the end flange 30, welding is accomplished by application of frequencies in the ultrasonic range while simultaneously pressing the filter card against the end flange whereby the ultrasonic energy is concentrated at the tapered edges 62 to cause them to become molten and to bond firmly to the paper filter. In this way, the ribs are locked to firmly embedded into the surface of the filter card without otherwise altering the characteristics of the filter. The mere application of ultrasonic welding is insufficient to secure the filter card to the end flange without energy directors at appropriately spaced intervals which serve to permanently affix or attach the filter card to the end flange as described. This form of positive attachment achieves more accurate alignment between the card and end flange so as to assure that the openings between the port and filter card are aligned for unobstructed flow of the liquid therethrough and greatly facilitates loading of the chamber and attached filter card in place within the holder assembly preliminary to each centrifuge operation. Most importantly, the attached filter card avoids reuse of the card or assembly, since any attempt to remove the filter card will leave substantial segments in surrounding relation to the ribs and preclude proper placement and positioning of a fresh filter card over the end flange of the chamber. Attachment in the manner described also minimizes any danger of smearing or loss of the deposit on the slide when the holder assembly is removed from the carrier plate and the slide is separated from the filter card and chamber for analysis.

Figure 7:
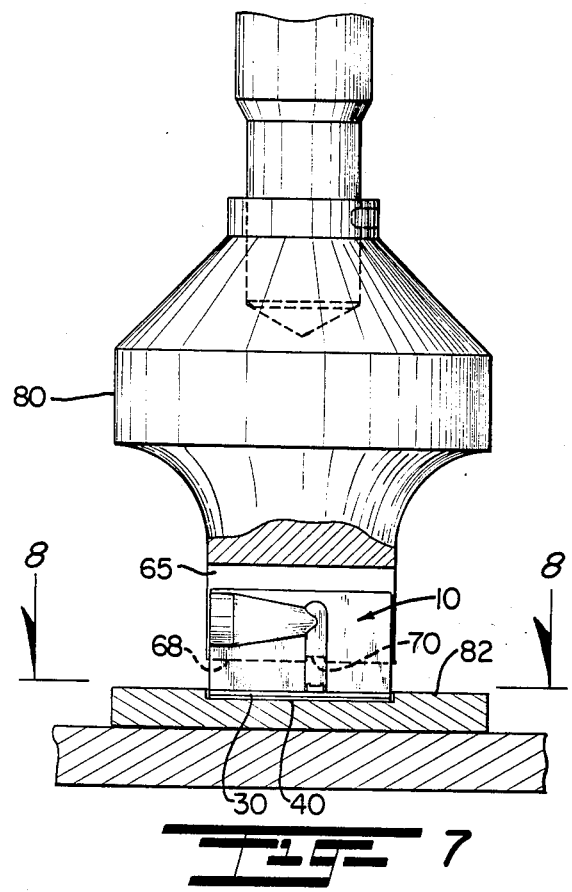
FIG. 7 is an enlarged view in more detail of the welding unit illustrated in FIG. 6 and with the welding horn shown partially in section.
Figure 8:
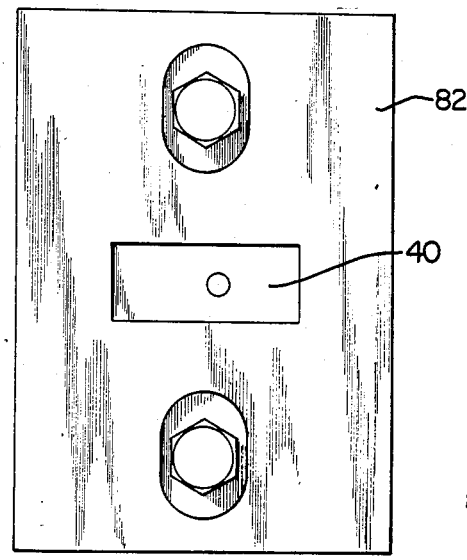
FIG. 8 is a view taken about lines 8—8 of FIG. 7 and illustrating the placement of the filter card on a portion of a jig.
Figure 9:
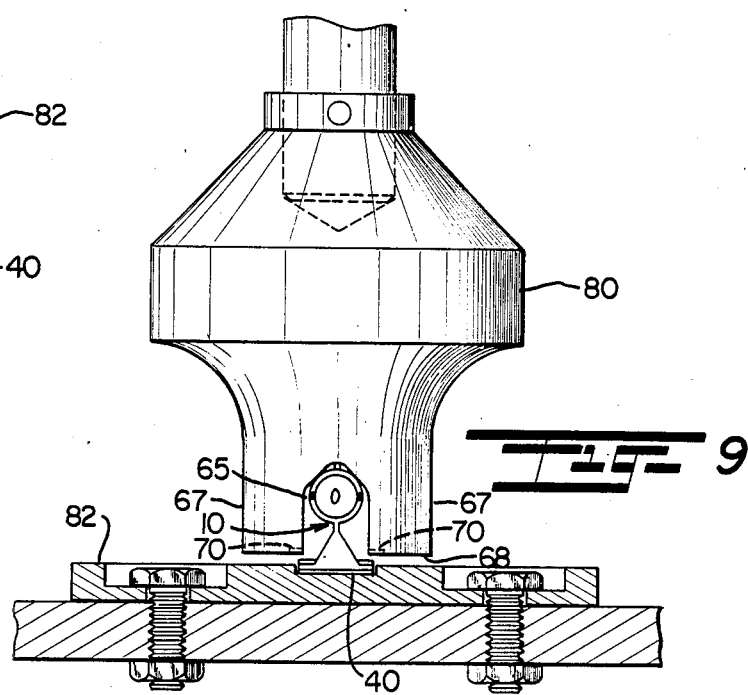
FIG. 9 is an end view partially in section of the welder unit and jig shown in FIG. 7.

In the preferred method of welding and affixing a filter card 40 to an end flange 30 of chamber 10, as illustrated in FIGS. 6 to 9, the chamber 10 is inserted within a cavity 65 of a welding horn 80. A filter card 40 is placed into position on a jig 82 beneath the exposed or lower end surface of the flange 30. The welding horn 80 is specifically designed to be of generally U-shaped configuration with downwardly directed legs 67 terminating in lower end surfaces 68, the horn 80 being superimposed over the chamber 10 until the end surfaces 68 are disposed in close proximity to the front or upper surface of the end flange 30 on the side opposite to the filter card 40. Slots 70 are formed in the end surfaces 68 of the horn 80 to register with the ledges 33 on the end flange 30 thereby permitting the end surfaces 68 of the horn to bear against the flat surface of the flange. Ultrasonic energy is then applied to the horn via a standard welding unit as generally designated at W for a very short duration or interval of time on the order of less than one second which is more than sufficient to heat the energy directors 60 to a level and to cause their edges 62 to become molten and to bond to the filter without burning the filter paper. The horn is then removed followed by removal of the completed chamber assembly from the cavity. A preferred form of ultrasonic welder is a Model 8400 horn with a gold booster manufactured and sold by Branson Sonic Power Company of Dansbury, Conn. It should be appreciated that the tapered edges 62 of the energy directors or ribs 60 permit sufficient concentration of heat to cause the edges to be rapidly heated to a molten state without burning the filter paper itself. In this relation, other cross-sectional configurations may be adopted or employed to accomplish the same end; and, for example, the cross-sectional configuration of the ribs may be rounded or provided with multiple edges so long as there is sufficient concentration of heat to cause the desired bonding without unduly heating the paper filter. Moreover, the location of the ribs may be varied to some extent, bearing in mind that the ultrasonic welder must be applied to the surface of the end flange directly opposite to the ribs in order to most rapidly direct the energy into the ribs 60 for welding purposes and therefore are most desirably located along opposite side edges so as to be aligned opposite to the points of contact between the ribs 60 and filter card 40.

It is therefore to be understood that various modifications and changes may be made in the unitary chamber and filter unit and method of making same without departing from the spirit and scope of the present invention as defined by the appended claims.

I claim:

1. A unitary disposable filter unit adapted for use in the analysis of body fluids comprising:
    a disposable sample chamber having a liquid sample-receiving funnel, a flat solid flange member defining a support surface for a filter card and a discharge port extending from said funnel and terminating in an opening in said flange member;
    a filter card overlying said support surface of said flange, said filter card including an opening therein; and
    securing means for permanently affixing said filter card to said support surface with said opening in said card aligned with said discharge port whereby said filter card is integrally united to said support surface and cannot be removed from said support surface without leaving segments of said filter card attached to said support surface.

2. A filter unit according to claim 1, said flange member having attachment ribs protruding from said support surface at spaced intervals therealong and embedded in said filter card.

3. A filter unit according to claim 2, said ribs on said flange member disposed at the outer peripheral edges of said support surface on said flange member, and said securing means operative to permanently affix said filter card to said ribs.

4. A filter unit according to claim 3, said flange member being generally rectangular and said ribs disposed adjacent to each corner of said flange member in facing relation to said filter card.

5. A filter unit according to claim 2, said ribs terminating in tapered edges defining energy directors adapted for application of ultrasonic energy thereto.

6. A filter unit according to claim 5, said ribs being of narrow elongated configuration and bonded to corresponding corners of said filter card.

7. In a centrifuge wherein a plurality of filters are mounted on a rotating carrier, each said holder having clamping means for releasably receiving a cytology chamber and a microscopic slide therein, the improvement comprising:
    said cytology chamber defined by a disposable sample chamber having a liquid sample-receiving funnel and an end flange with a discharge port extending between said funnel and said flange;
    a filter card overlying said end flange including an opening therein; and
    securing means for permanently affixing said filter card to said end flange with said opening in said card aligned with said discharge port whereby said filter card is integrally united to said end flange and cannot be removed from said end flange without leaving segments of said filter card attached to said end flange, each said chamber positioned in one of said holders, and said clamping means releasably clamping said slide in overlying relation to said filter card.

8. In a centrifuge according to claim 7, each said end flange of a sample chamber having ribs protruding from an exposed surface of said end flange at spaced intervals therealong and embedded in said filter card.

9. In a centrifuge according to claim 8, said ribs on each said end flange disposed at outer peripheral edges of said flange.

10. In a centrifuge according to claim 9, said flange being generally rectangular and said ribs disposed adjacent to each corner of said flange.

11. In a centrifuge according to claim 8, said ribs on each said flange defining energy directors adapted for application of ultrasonic energy thereto.

12. In a centrifuge according to claim 11, said ribs being of narrow elongated configuration and ultrasonically welded to corresponding corners of said filter card.

13. In a centrifuge according to claim 7, said securing means characterized by bonding said filter card to said end flange at spaced intervals along outer edges thereof.

14. A unitary disposable filter unit for use in analysis of body fluids comprising a disposable sample chamber having a liquid sample-receiving funnel, a flat solid flange member defining a support surface for a filter card and a discharge port extending from said funnel and terminating in an opening in said flange member; and a filter card overlying said support surface of said flange including an opening therein, said filter unit formed by the steps of:
    forming energy directors on said support surface in spaced relation to said discharge port;
    placing said filter card in overlying relation to said support surface with the opening in said filter card aligned with said discharge port; and
    applying ultrasonic energy to said end flange whereby to weld said energy directors to said filter card so that said filter card is integrally united to said support surface and cannot be removed therefrom without leaving segments of said filter card attached to said support surface.

15. A unitary disposable filter unit according to claim 14, characterized by the step of locating said energy directors at spaced intervals around outer peripheral edges of said support surfaces and pressing said filter card against said support surface as ultrasonic energy is applied to the surface of said end flange opposite to said support surface.

16. A unitary disposable filter unit according to claim 15, said energy directors being in the form of attachment ribs protruding from said support surface and terminating in tapered edges defining said energy directors for the application of ultrasonic energy thereto.

* * * * *